United States Patent [19]

Wienecke et al.

[11] Patent Number: 4,626,427
[45] Date of Patent: Dec. 2, 1986

[54] CARDAMOM SEED PREPARATION BEING EFFECTIVE AGAINST BAD BREATH

[75] Inventors: Horst G. P. Wienecke, Gross-Gerau; Karl-Wilhelm Stock, Buettelborn, both of Fed. Rep. of Germany

[73] Assignee: Richardson-Vicks Inc., Wilton, Conn.

[21] Appl. No.: 776,678

[22] Filed: Sep. 16, 1985

[30] Foreign Application Priority Data

Oct. 15, 1984 [DE] Fed. Rep. of Germany ....... 3437679

[51] Int. Cl.$^4$ ................................................ A61K 9/36
[52] U.S. Cl. ........................................ 424/35; 424/58; 424/195.1; 426/93; 426/309; 514/738; 514/777; 514/959; 514/960
[58] Field of Search ................ 424/35, 58, 195.1; 426/93, 309; 514/195.1, 738, 777, 959, 960

[56] References Cited

U.S. PATENT DOCUMENTS

| | | | |
|---|---|---|---|
| 69,393 | 10/1867 | Blake | 424/58 |
| 127,408 | 6/1872 | Farnham | 424/58 |
| 207,013 | 8/1878 | Carter | 424/35 |
| 352,466 | 11/1886 | Huttemeyer | 424/35 |
| 1,527,523 | 2/1925 | Nitardy | 424/58 |
| 1,891,698 | 12/1932 | Tuvin | 424/35 |
| 2,778,045 | 1/1957 | Bly | 424/58 |
| 3,395,213 | 7/1968 | Rieckmann | 424/35 |
| 3,554,767 | 1/1971 | Daum | 424/35 |
| 3,914,434 | 10/1975 | Bohni | 514/738 |
| 4,053,650 | 10/1977 | Chino | 426/309 |
| 4,146,653 | 3/1979 | Mader | 424/35 |
| 4,161,545 | 7/1979 | Green | 426/309 |
| 4,169,885 | 10/1979 | Raaf | 424/35 |
| 4,374,824 | 2/1983 | Wahmi | 424/58 |
| 4,423,030 | 12/1983 | Hayes | 424/58 |
| 4,501,758 | 2/1985 | Morris | 426/93 |
| 4,511,553 | 4/1985 | Boesig | 426/309 |
| 4,515,820 | 5/1985 | Tang | 426/309 |
| 4,522,833 | 6/1985 | Sharma | 426/93 |

FOREIGN PATENT DOCUMENTS

| | | | |
|---|---|---|---|
| 2426916 | 1/1976 | Fed. Rep. of Germany | 424/58 |
| 2143622 | 2/1973 | France | 424/58 |
| 59-163305 | 9/1984 | Japan | 424/58 |
| 59-163308 | 9/1984 | Japan | 424/58 |

OTHER PUBLICATIONS

Pereira, Materia Medica & Therapeutics, 3rd Ed. (1854), Blanchard & Lea, Phila., Pa., vol. II, pp. 240–251.
U.S.D., 24th Ed. (1941), Part I, pp. 229–231, Cardamom Seed, U.S.P. Hocking Dictionary of Terms in Pharmacognosy (1955), C. C. Thomas, pp. 6, 41, 75, 250.
Hirschorn, The Home Herbal Doctor, p. 41.
Pritzker, Pharm. Acta Helv., 19: 47–51, 76–80, 106–111 (1944).
Sreenivasamurthy, Food Sci. (Mysore) 8: 284–294 (1959).
Mogens, Dansk Tidsskr. Farm., 40(5): 156–163 (1966).
Krishnamurthy, J. Food Sci. Technol., 4(4): 170 (1967).
Shankaracharya, Indian Food Packer, 25(5): 28–36 (1971).
Mathai, J. Sci. Food Agric., 36(6): 450–2 (1985).
Kumara, J. Sci. Food Agric., 36(6): 491–8 (1985).

*Primary Examiner*—Shep K. Rose
*Attorney, Agent, or Firm*—Salvatore R. Conte

[57] ABSTRACT

Preparation being effective against bad breath, particularly caused by strongly smelling food stuffs or cigarettes, alcohol and the like, consisting of cardamom seeds which are individually or jointly coated by a shell mass comprising a sugar mass or the like.

5 Claims, No Drawings

CARDAMOM SEED PREPARATION BEING EFFECTIVE AGAINST BAD BREATH

Subject matter of the invention is a preparation being effective against bad breath.

There are various reasons for bad breath. Firstly, it can be caused by bacterial or enzymatic degradation of food particles in the oral cavity or by generally bad state of the dentures. Here the reason for development is directly in the oral cavity itself. But it may also occur after the consumption of strong smelling food stuffs, like onions or garlic, or from consumption of alcohol. Here the bad breath originates in the stomach.

Against the unpleasant smells developing in the oral cavity numerous measures can be taken, like regular dental care several times a day with tooth brush and tooth paste, mouth rinses, the consumption of chewing gum or the sucking of special products.

To eliminate or reduce the bad breath, originating from the stomach, there exist largely only products that can be given in doses, and basing on the effectiveness of chlorophyll. However, these products do not contain natural chlorophyll which is difficultly soluble, thus, they are not purely natural products for the designated purpose but are sodium or potassium salts of the chlorophyll, obtained by cautious alkaline hydrolysis, and designated as chlorophyllines. After administration they effect a perceptible odour reduction and exhibt this effect principally also in the oral cavity. However, since they lead to long-lasting discolourations of the oral mucosa and the teeth they can be used there only in very small concentrations. E.g. there are tooth pastes that contain from 0.2 to 0.5% of chlorophyllines.

A preparation suitable for reducing bad breath, originating from the oral cavity as well as for that originating from the stomach, and preferably containing natural starting materials is not known.

It has been found that the seed of the cardamom plant, which in powder form is used as spice, is suitable to reduce the bad breath originating in the oral cavity as well as that originating from the stomach, if it is chewed and then swallowed. Since the seed is a natural product, the individual seed is either covered by a shell mass (dragee pearls) or a certain amount of seeds is worked into this shell mass (chewing bonbon) to prevent spoiling of the seeds and to facilitate dosage and administration. The shell mass consists of sugar, sugar substitutes, like sorbit (sorbitol xylite (xylitol) and the like, or their combination. Preferably aromatics, like peppermint oil or other essential oils are added to the shell mass to increase the smell reducing effect in the oral cavity.

The administration, even with regard to dosage, is in both cases easy and the effect is surprisingly good. One takes about six dragee pearls or one chewing bonbon, containing 6 seeds, sucks and chews these and then swallows the chewed mass.

The invention is explained by the following examples:

EXAMPLE 1

450 g of gelatine are mixed with 570 g of water and left to swell for about 20 min. Then the mass is heated to about 45° C. and 900 g of dextrose monohydrate, 1125 g of glucose syrup, 336 g of coconut fat, and 63 g of nurupas (as emulgator) are added. This mixture is added to a mixture consisting of 9.750 kg of sugar and 10.5 kg of glucose syrup in 3 l of water which have been heated to 134° C. To this mixture are further added 1.5 kg of coconut fat, 1.5 kg of powdered sugar, 60 ml of peppermint oil, and 300 g cardamom seeds. After mixing this mass well and cooling it down to about 35° C. all of the mass is drawn by an extruder, customarily used for the preparation of a hard bonbon mass, to work in air. The mass so treated is then fed to an extruder connected with a cutter and a coiling machine. Thereby squares of about 5 g each are obtained, containing an average of 6 cardamom seeds. The yield in these chewing bonbons is about 5,000 pieces.

EXAMPLE 2

1 kg cardamom seeds are put into a coating vessel and coated step by step in a manner known per se with an aromatized sugar solution of the following composition, until a weight of 200 mg per individual pearl has been reached:

water: 25%=5 liter
sugar: 73.9%=14.780 kg
peppermint oil: 1.1%=220 g

Before the last coats are applied 0.02% of chlorophylline (E 141) is addded to the aromatized sugar solution to obtain a green colouration. The final yield comprises 100,000 (=20 kg) slightly green coloured dragees (pearls), containing each one cardamom seed.

The effectivity of the preparation according to the invention for combatting bad breath, originating from the consumption of onions, garlic, cigarettes and alcohol, has been tested as follows:

Groups of 12 persons each were formed and to two each of the said groups of persons were administered per person 1 ml onion or garlic juice, 237 ml warm beer or they were told to smoke two cigarettes without filter. The strength of the breath immediately after the consumption of the smelling substances and subsequently in certain periods of time has been determined according to the following scale and a mean value has been calculated from the individual values. To one group of persons for each of the four categories of smells immediately after administration of the smelling substances and then again after 120 minutes, every time after evaluation, 6 pearls of the preparation prepared according to example 2 were administered. The average values of the test groups and the untreated control groups are found in Table I:

Scale of evaluation:
0=no smell
2=smell barely perceptible
4=smell well perceptible
6=strong smell
8=very strong smell

TABLE I

| | Average smell time (in minutes) | | | | | | |
|---|---|---|---|---|---|---|---|
| | 0 | 15 | 30 | 45 | 60 | 120 | 480 |
| Onion (control) | 7.5 | 7.0 | 7.0 | 6.4 | 6.4 | 6.4 | 6.0 |
| Onion (treated) | 7.5 | 3.6 | 3.4 | 3.0 | 3.0 | 3.0 | 0.5 |
| Garlic (control) | 8.0 | 8.0 | 7.4 | 7.0 | 7.0 | 7.0 | 6.4 |
| Garlic (treated) | 8.0 | 3.2 | 3.0 | 3.0 | 3.0 | 2.8 | 0.8 |
| Alcohol (control) | 7.6 | 7.2 | 7.0 | 6.4 | 6.0 | 5.4 | 5.0 |
| Alcohol (treated) | 7.6 | 2.8 | 2.4 | 2.0 | 2.0 | 1.8 | 0.0 |
| Tobacco (control) | 7.5 | 7.0 | 7.0 | 6.4 | 6.4 | 6.0 | 5.8 |
| Tobacco (treated) | 7.5 | 3.0 | 2.4 | 2.4 | 2.4 | 2.0 | 0.0 |

We claim:
1. Preparation being effective, when chewed and swallowed, against bad breath originating from the consumption of smelling substances, including onions, garlic, alcohol and smoking tobacco, characterized in that it comprises a chewing bonbon containing uncoated seeds of the cardamom plant, or cardomom seeds coated by a dragee shell mass, said chewing bonbon and said drageee shell mass consisting essentially of sugar or sugar substitutes including sorbit, xylite, and mixtures thereof.

2. Preparation according to claim 1, characterized in that each seed is individually coated by the shell mass.

3. Preparation according to claim 1, characterized in that more than one seed are jointly coated by the shell mass.

4. Preparation according to claim 1, characterized in that aroma is added to the shell mass.

5. Preparation according to claim 4, characterized in that the aroma is peppermint oil.

* * * * *